(12) United States Patent
Margraf et al.

(10) Patent No.: US 10,052,414 B2
(45) Date of Patent: Aug. 21, 2018

(54) METHOD AND APPLICATOR FOR THE PERIOPERATIVE DISINFECTION OF MEDICAL INSTRUMENTS TO BE INSERTED THROUGH NON-NATURAL OPENINGS

(71) Applicants: Stefan Margraf, Frankfurt (DE); Jan Stange, Rostock (DE)

(72) Inventors: Stefan Margraf, Frankfurt (DE); Jan Stange, Rostock (DE)

(73) Assignee: Solvamed GmbH, Frankfurt (DE)

( * ) Notice: Subject to any disclaimer, the term of this patent is extended or adjusted under 35 U.S.C. 154(b) by 788 days.

(21) Appl. No.: 14/373,488

(22) PCT Filed: Jan. 22, 2013

(86) PCT No.: PCT/DE2013/000039
§ 371 (c)(1),
(2) Date: Jul. 21, 2014

(87) PCT Pub. No.: WO2013/107443
PCT Pub. Date: Jul. 25, 2013

(65) Prior Publication Data
US 2014/0370067 A1    Dec. 18, 2014

(30) Foreign Application Priority Data

Jan. 22, 2012 (DE) .................. 10 2012 001 216

(51) Int. Cl.

| | | |
|---|---|---|
| A61L 29/16 | (2006.01) | |
| B05C 1/06 | (2006.01) | |
| A61L 29/08 | (2006.01) | |
| A61L 31/16 | (2006.01) | |
| A61M 25/01 | (2006.01) | |
| A01N 43/40 | (2006.01) | |
| A61M 25/00 | (2006.01) | |

(52) U.S. Cl.
CPC .............. *A61L 29/16* (2013.01); *A01N 43/40* (2013.01); *A61L 29/08* (2013.01); *A61L 31/16* (2013.01); *A61M 25/0111* (2013.01); *B05C 1/06* (2013.01); *A61L 2202/15* (2013.01); *A61L 2202/24* (2013.01); *A61L 2300/404* (2013.01); *A61L 2300/606* (2013.01); *A61L 2420/02* (2013.01); *A61L 2420/06* (2013.01); *A61M 2025/0056* (2013.01)

(58) Field of Classification Search
CPC ....... A61M 25/0111; A61M 2025/0056; A61L 29/16; A61L 29/08; A61L 2300/606; A61L 2202/24; A61L 2202/15; A61L 2420/02; A61L 2300/404; A61L 2420/06; A61L 31/16; B05C 1/06; A01N 43/40
See application file for complete search history.

(56) References Cited

U.S. PATENT DOCUMENTS

| | | | |
|---|---|---|---|
| 4,353,367 A | 10/1982 | Hunter et al. | |
| 5,015,228 A | 5/1991 | Columbus et al. | |
| 8,550,737 B2 * | 10/2013 | Ruiz, Sr. .......... | A61B 17/00491 401/133 |
| 2006/0051384 A1 * | 3/2006 | Scholz .................... | A01N 37/02 424/405 |
| 2006/0052744 A1 * | 3/2006 | Weber ..................... | A61L 27/34 604/48 |
| 2009/0060624 A1 * | 3/2009 | Schenck .................. | A61C 5/62 401/171 |
| 2009/0234177 A1 * | 9/2009 | Lebovic ................ | A61N 5/1016 600/6 |
| 2010/0322699 A1 | 12/2010 | Dam | |

FOREIGN PATENT DOCUMENTS

| | | | | |
|---|---|---|---|---|
| CN | 1761493 A | | 4/2006 | |
| DE | 198 30 421 A1 | | 1/2000 | |
| DE | 19830421 A1 | * | 1/2000 | ......... A61F 13/0213 |
| DE | 100 38 521 A1 | | 2/2002 | |
| DE | 20 2010 006 090 U1 | | 9/2010 | |

(Continued)

OTHER PUBLICATIONS

International Search Report for parent PCT application WO2013107443 A1, dated Jun. 26, 2013.

(Continued)

*Primary Examiner* — Michael G Hartley
*Assistant Examiner* — Nabila G Ebrahim
(74) *Attorney, Agent, or Firm* — William Gray Mitchell

(57) ABSTRACT

The invention relates to means and methods for the disinfection of an insertion channel to prevent in particular catheter sepsis, which significantly reduces the carry-over of germs even out of deeper skin layers by means of medical instruments, such as catheters, to be introduced into non-natural openings and also permits the decontamination of perioperatively contaminated medical instruments. The disinfection of the insertion channel is achieved by means of a method for the perioperative coating of a medical instrument to be inserted into an invasively produced bodily opening before use, comprising the application of a preferably viscous or foam-like composition containing at least one anti-infective compound, preferably a gel having octenidine, by means of an applicator, such that when said gel is used, the composition is also specifically effective in the first millimeters of the insertion channel. Furthermore, an immediate disinfecting action is provided over the entire coated surface.

14 Claims, 7 Drawing Sheets

(56) References Cited

FOREIGN PATENT DOCUMENTS

| EP | 1 982 696 A1 | 10/2008 |
|----|---|---|
| FR | 2 956 978 A1 | 9/2011 |
| GB | 2 429 634 A | 3/2007 |
| WO | WO 00/33895 A1 | 6/2000 |
| WO | WO 01/28515 A1 | 4/2001 |
| WO | WO 02/074350 A1 | 9/2002 |

OTHER PUBLICATIONS

Chinese Office Action dated Jun. 23, 2015 in corresponding CN application No. 201380012062.8.

* cited by examiner

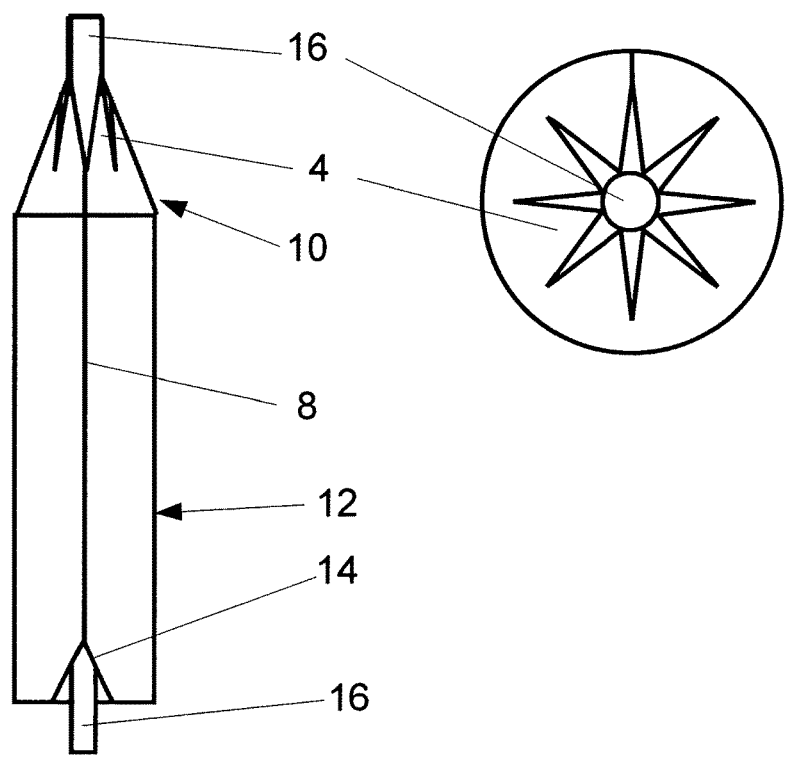
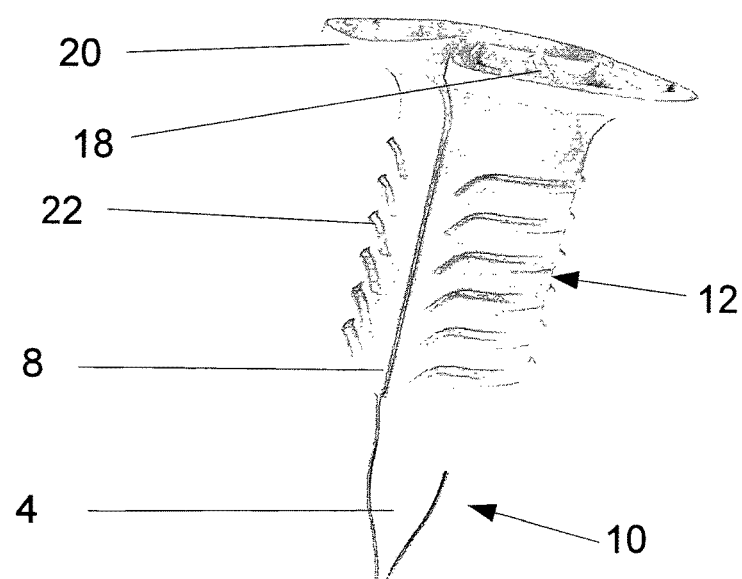

METHOD AND APPLICATOR FOR THE PERIOPERATIVE DISINFECTION OF MEDICAL INSTRUMENTS TO BE INSERTED THROUGH NON-NATURAL OPENINGS

CROSS REFERENCE TO RELATED APPLICATIONS

This patent application claims priority International Patent Application PCT/DE2012,000039, filed on Jan. 22, 2013 and German Patent Application 10 2012 001 216.0, filed on Jan. 22, 2012.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The present invention relates to a method and an applicator for the perioperative disinfection of medical instruments to be inserted through non-natural openings.

Background of the Invention

The current state of knowledge is as follows.

A large percentage of the group of sepsis infections caused by medical instruments represent diseases and fatalities caused by catheter sepsis, and they are included in the group of theoretically preventable hospital infections within the scope of the treatment of other severe diseases of patients. In Germany alone, it is assumed that they result in several thousand fatalities, leading to costs in the billions.

In light of the scope and the consequences of catheter sepsis there is an urgent need to develop improved methods and means to reduce infections and fatalities associated with catheter sepsis.

The problem of catheter sepsis is essentially caused by the fact that only the surface of the skin is disinfected when catheters are placed, and no methods or preparations are known to also disinfect the insertion channel, where most germs originate, which then contaminate the catheter. Here, deeper skin layers with hair follicles, sebaceous glands and sweat glands also contain germs not reached by surface disinfectants. In particular the problem of entraining germs from deeper skin layers has previously not been solved.

The present invention provides methods and means for the first time which prevent the transfer of fertile germs from the insertion channel to medical instruments and this way fight catheter sepsis.

The application of antiseptically acting chlorhexidine-coatings is already known for catheters. The catheters are already provided with a final coating during their production. The coating is very costly, with a surcharge of USD 30-40 compared to uncoated catheters, thus it is available for a minority of catheters only. At the moment of penetrating the skin the catheter is dry; however in the dry state the coating is ineffective. Accordingly, in spite of such coating, biofilms carrying germs can develop on the catheter.

The product Instillagel is known: a viscous gel for the application in catheterizations of the urinary tract. It is used to provide local anesthesia (lidocaine) and lubrication, and it includes chlorhexidine in an ineffective dosage (0.05%) in a cellulose gel base. It is neither intended nor licensed for the application in vascular catheters. Further, the product Tegaderm CHG is known, which represents a bandage to cover the insertion site of a placed catheter. The product includes a solid gel plate, from which chlorhexidine (2%) is released over an extended period of time in order to prevent an infection at the skin site, from which the catheter projects. It is therefore neither capable of nor intended for preventing any contamination of the catheter during the catheter placement, which may lead to blood sepsis. Additionally, it is only used after the placement of a catheter has already occurred.

The document U.S. Pat. No. 5,015,228 discloses a gel bandage which sterilizes the skin surface at the insertion site as well as the syringe prior to taking fluids (blood) from human vessels or prior to supplying liquids (drugs). This gel bandage also includes a solid gel plate containing disinfectants. However, the substances provided for disinfection in U.S. Pat. No. 5,015,228 are suitable only under certain conditions, because either they require too much time for developing their disinfecting effects and/or they should not enter the body (lack of tolerance). This gel bandage is disadvantageous in that it additionally would aggravate the discovery of veins, because it represents an additional solid layer on the skin, although thin and transparent, which compromises the feeling and visual detection of the vein to be punctured. Furthermore, when penetrating the gel the needle might potentially become clogged by the gel punched out.

The document DE 198 30 421A1 describes a device for treating and caring for the edge sections of artificial body openings and/or the area between the skin of the patient and medical instruments inserted therein (e.g., catheters, fastening screws, tubes) as potential access sites for germs. The device is provided for the use after the placement of a medical instrument.

The disclosure includes a plastic disk to be adhered on the skin as a boundary of the access site (wound) against contaminating influences from the atmosphere, as well as an opening for e.g., an antiseptic gel or a paste, which keeps the skin moist near the access site and may include antiseptic agents which have a disinfecting effect upon the wound. The device disclosed in DE 198 30 421 serves for protection after a surgical procedure in order to support wound healing and to prevent subsequent contamination of the access site from the outside (by external influences).

WO2000033895 discloses cysteine derivatives, such as N-acetyl cysteine, in context with antibiotics for the therapy of biofilms in catheters.

In the U.S.A., (on an annual basis) in 15 million treatment days using central venous catheters (also: central venous catheter (CVC) days) in intensive care units, 80,000 infections in the blood stream caused by catheters (catheter-related blood stream infections (CRBSI)) occur in intensive care units, thus approximately 5.3 infections per 1000 CVC days. This is equivalent to estimated approximately 250,000 infections of the blood stream (also called blood stream infections (BSI)) from all the hospital wards incl. intensive care units (see Guidelines for the Prevention of Intravascular Catheter-related Infections, CID 2011:52; O'Grady et al.). This causes USD 20,000 (Warren, 2006)-

33,000 (Mermel, 2000) additional costs per infection, which adds to USD 5-8 billion of total annual costs. The human loss is paid in 24,300 fatalities per year (2006) (Wenzel R. and Edmond M. N Engl J Med 2006; 355: 2781-2783). In Germany, in 4.7 million CVC-days in inventive care units, 12,000 infections of the blood stream caused by catheters occur (also: catheter-related blood stream infections (CRBSI)), with an increasing trend between the years 2000 and 2008 (1.8; 2; 2.5 and/or 2.6/1000 CVC-days (KISS, Petra Gastmeier)). However, it must be assumed that these numbers are incomplete, because the majority of reports occur on a voluntary basis (personal opinion of Dr. Geffers, KISS). Catheter sepsis causes 6,000-10,000 fatalities per year in Germany.

In the group of endoscopic surgeries, arthroscopies alone are suspected to carry a probability of infection from 0.2 to 0.4%. Here, staphylococci of the skin flora are the primary causes.

The germs occurring most frequently in catheter sepsis include germs of the normal skin flora, such as coagulant negative staphylococci (most common germ in central venous catheter sepsis) as well as *enterococcus* spp., *proteus* spp., *P. aerugionsa, klebsiella* spp., *S. aureus*, including MRSA, *enterobacter* spp. and *E-coli*.

Only the surface of the skin can be disinfected. However, deeper layers, particularly hair follicles with sebaceous glands or sweat glands, also include germs which can only be reached by disinfectants to an insufficient extent and thus can transfer to the catheter upon placement thereof. Essentially for this reason, for example approximately 10% of all blood cultures are false negatives.

In the context with foreign objects, such as catheters, the transfer of just a few germs is very dangerous. Elek and Conen[2] demonstrated in 1957 that merely 100 staphylococci (*pyogenes*) associated at a foreign object (here: suture material) trigger severe infections in the skin of healthy persons. Contrary thereto, more than 1 million germs were tolerated without any foreign objects. This shows that a very small germ count can lead to severe infections in context with foreign objects.

Furthermore, operating rooms are not sterile, but only show low germ counts. Accordingly, airborne infections and smear infections occur, which can contaminate a catheter.

Today, catheterizations are generally performed in the operating room. Essentially, the puncture site is disinfected. It is performed primarily with alcohol-based disinfectants, in rarer cases with a water-based PVP-iodine. With this method approximately 99% of the germs on the surface of the skin are deactivated[3].

The alcohol-based disinfectants may include other disinfecting compounds in addition to alcohol, such as chlorhexidine digluconate (in the following called "chlorhexidine") or octenidine hydrochloride (in the following called "octenidine").

In light of the scope and the consequences of catheter sepsis, it is urgently necessary to develop improved methods and means to reduce infections and fatalities associated with catheter sepsis. In particular, no solution has been found up to now in prior art for the problem of transferring germs from deeper skin layers. Additionally, so far there is no solution for the problem that catheters, after removal from the packaging, can be contaminated with bacteria and are then administered in this state.

BRIEF SUMMARY OF THE INVENTION

In a preferred embodiment, a method for the perioperative disinfection of a medical instrument to be inserted into an invasively generated body opening, preferably a vascular catheter, and/or an injection channel generated by inserting a medical instrument into the body, comprising the application of a viscous or foam-like composition containing at least one anti-infectious compound upon the medical instrument prior to use, wherein the composition is embodied to adhere on the medical instrument like a film after being brought into contact with the medical instrument, and that at least a portion of the composition adhering like a film reaches at least to the epidermis upon insertion of the medical instrument into the body.

In another preferred embodiment, the method as described herein, wherein the composition is in the form of a gel.

In another preferred embodiment, the method as described herein, with the anti-infectious composition being applied via an applicator.

In another preferred embodiment, the method as described herein, wherein the medical instrument is a vascular catheter, an endoscope, a drainage, a peritoneal catheter, a pin, a trocar, or an electrode.

The method according to claim 1, wherein the anti-infectious compound is selected from the group consisting of octenidine and chlorhexidine or a combination thereof.

In another preferred embodiment, the method as described herein, wherein the composition further comprises an anti-infectious compound selected from the group consisting of hydrogen peroxide, povidon-iodine, cetylpyridinium chloride, cetylpyridinium bromide, 2-phenoxy ethanol, triclosan, polyhexanide, ethyl alcohol, isopropanol, bacitracin, gramicidin, fusidinic acid, polymyxine B, neomycin, gentamycin, erythromycin, chloramphenicol, lincosamide, minocycline, rifampin, doxycycline, or a gyrase inhibitor, or a combination thereof.

In another preferred embodiment, the method as described herein, wherein the composition being provided as PAA, preferably carbomer, or PVA gel, with the PAA portion ranging from 0.1 to 2% by weight and the PVA-portion ranging from 0.1 to 20% by weight.

In another preferred embodiment, the method as described herein, wherein the composition further comprises polyvinyl pyrrolidone from 0.1 to 5% by weight.

In another preferred embodiment, the method as described herein, wherein the composition comprises octenidine from 0.01 to 0.2%.

In another preferred embodiment, the method as described herein, wherein the medical instrument is inserted into an invasively generated body opening being intended for an extended stay in the body.

In another preferred embodiment, a composition comprising at least one anti-infectious compound, wherein the composition is embodied to adhere like a film on the medical instrument upon being brought into contact with a medical instrument to be inserted preoperatively into an invasively generated body opening, and that at least a portion of the composition adhering like a film reaches at least the epidermis upon inserting the medical instrument into the body.

In another preferred embodiment, the method of use of the composition described herein, comprising the step of applying the composition for the perioperative disinfection or washing of medical instruments to be inserted into invasively generated body openings or as an anti-adhesive or lubricant on medical instruments to be inserted into invasively generated body openings or for disinfecting an insertion channel generated by inserting a medical instrument into the body.

In another preferred embodiment, a medical instrument to be inserted into invasively generated body openings, from the group comprised of a vascular catheter, endoscope, pin, trocar, or electrode, with a preferably viscous or foam-like composition comprising an anti-infectious compound, such compound selected from the group comprised of chlorhexidine and octenidine, wherein the composition is embodied to adhere on the medical instrument like a film upon being brought into contact with it and that the film-like adhesive composition, upon inserting the medical instrument, reaches into the body at least to the epidermis.

In another preferred embodiment, a method for the production of at least one composition comprising an anti-infectious compound for the perioperative disinfection of a medical instrument to be inserted into an invasively generated body opening or for the disinfection of an insertion channel generated by the insertion of a medical instrument into the body, comprising the steps of:
(a) producing a gel, preferably a PAA, or PVA gel in $H_2O$ with a pH ranging from 5 to 8,
(b) dissolving an anti-infectious substance selected from octenidine and chlorhexidine in polyvinyl pyrrolidone, and
(c) mixing the gel of (a) with the solution of (b) so that the PAA is present in the gel at a range from 0.1 and 2% by weight and PVA at a range from 0.1 and 20% by weight, the anti-infectious substance at a concentration from 0.01 to 2% by weight, and the polyvinyl pyrrolidone at a concentration from 0.1 to 5% by weight.

In another preferred embodiment, an applicator for the perioperative disinfection of a medical instrument to be inserted into invasively generated body openings, with the applicator being embodied such that a viscous or foam-like, anti-infectious composition can be applied on a surface of the medical instrument by a relative motion between the applicator and said medical instrument, wherein the applicator, preferably located in the rear in the direction of motion, comprises a retention device for the anti-infectious compound, with the applicator being formed as an essentially hollow embodied reservoir with a conically tapering section, preferably located at the rear in the direction of motion.

In another preferred embodiment, the applicator as described herein, which comprises in an interior zone at least one reservoir or at least one carrier for the anti-infectious composition.

In another preferred embodiment, the applicator as described herein, with a cylindrical section following the conic section in the direction of motion.

In another preferred embodiment, the applicator as described herein, wherein the conically tapering section and/or the cylindrical section are open at the front end, seen in the direction of motion.

In another preferred embodiment, the applicator as described herein, with the retention device comprising an opening, which preferably is additionally slotted.

In another preferred embodiment, the applicator as described herein, with the conically tapering section comprising a multitude of slots, preferably embodied in the axial direction starting at the rear end of the conical section, seen in the direction of motion.

In another preferred embodiment, the applicator as described herein, with the conically tapering section essentially showing the form of a frustum.

In another preferred embodiment, the applicator as described herein, with a multitude of flexible tongues being formed by the slots.

In another preferred embodiment, the applicator as described herein, wherein the reservoir or the carrier are filled with a viscous, anti-infectious composition.

In another preferred embodiment, the applicator as described herein, with the applicator comprising laterally a slot, continuous in the axial direction.

In another preferred embodiment, the applicator as described herein, with the applicator preferably comprising an insertion aid for the medial instrument at the continuous slot extending laterally in the axial direction.

In another preferred embodiment, the applicator as described herein, wherein at least two engagement zones are provided at its exterior.

In another preferred embodiment, a kit comprising an applicator as described herein as well as an anti-infectious composition described in claim.

In another preferred embodiment, the kit as described herein, further comprising a medical instrument, preferably a vascular catheter.

In another preferred embodiment, a method of use of an applicator as described herein for applying a composition comprising at least one anti-infectious compound as described herein upon a medical instrument to be inserted into invasively generated body openings prior to use.

BRIEF DESCRIPTION OF THE DRAWINGS

FIG. 3a is a line drawing evidencing a side view and FIG. 3b is a line drawing evidencing a top view of an exemplary embodiment of FIG. 2 with an inserted medical instrument FIG. 4 is a line drawing evidencing a perspective illustration of a second exemplary embodiment

DETAILED DESCRIPTION OF THE INVENTION

Figure 1:
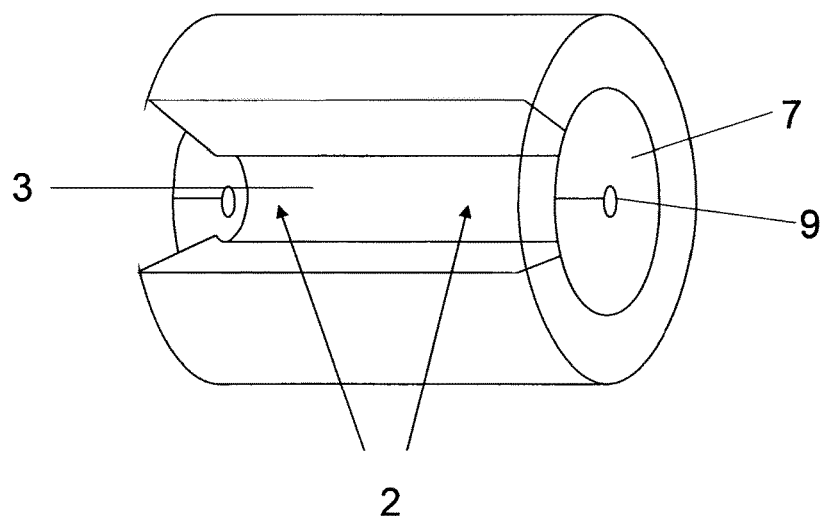
FIG. 1 is a line drawing evidencing a side view of an exemplary embodiment

The present invention provides means and methods to significantly reduce the transfer of germs even from deeper skin layers onto instruments to be inserted into non-natural openings, such as catheters, as well as additionally to improve the decontamination of preoperatively contaminated medical instruments, such as catheters, for example. Furthermore, the present invention allows an effective disinfection of an insertion channel generated by inserting a medical instrument into the body.

Unless stated otherwise, the parameters and features described for certain embodiments can also be applied to all other embodiments disclosed here. The statements made in % relate to % by weight, unless stipulated otherwise.

In one embodiment, the invention relates to a method for the perioperative disinfection of a medical instrument to be inserted into an invasively generated body opening, preferably a vascular catheter, comprising the application of a preferably viscous or foam-like composition containing at least one anti-infectious compound upon the medical instrument prior to use.

In particular, the invention relates to a method for the perioperative disinfection of a medical instrument to be inserted into an invasively generated body opening, preferably a vascular catheter, and/or an insertion channel generated by inserting a medical instrument into the body, comprising the application of a viscous or foam-like composition containing at least one anti-infectious compound upon the medical instrument prior to use, characterized in that the composition is embodied in order to adhere like a film on the medical instrument, after being brought into contact with the medical instrument, and that at least a portion of the film-like adhesive composition, upon insertion of the medical instrument into the body, reaches at least into the epidermis.

In the context with the present invention, "perioperative" shall be understood as the time immediately prior, during, and immediately after surgery, particularly immediately prior to surgery or immediately prior to the use of a medical instrument, e.g. prior to the placement of a catheter, particularly prior, during, or after an operation. Here, immediately represents a time lag from the surgery, i.e. the operation and/or the utilization of a medical instrument, of less than 1 h, less than 45 min., less than 30 min., less than 20 min., less than 15 min., less than 10 min., or less than 5 min., less than 2 min. or less than 1 min. In a period immediately prior to use of a medical instrument, e.g., during an operation, the above-mentioned time periods therefore relate to the time lag prior to the utilization of a medical instrument even within the scope of surgery.

Here, an invasively generated body opening represents a body opening naturally not present and generated by a surgical procedure, commonly in order to enable and/or for the purpose of executing a surgical procedure in the body. Examples of such invasively generated body openings are those for inserting medical instruments into blood vessels (e.g., catheters or permanent venous cannulas) or endoscopes for minimally invasive surgeries.

A medical instrument to be inserted into an invasively generated (or to be generated) body opening is preferably rod-shaped (with the diameter of its cross-section in reference to length showing a ratio of less than 1/10) and may also be flexible. The medical instruments to be used in the present invention pierce the skin during the insertion process into the body, which for this purpose is usually cut with a sharp blade, for example by a cannula. Examples of medical instruments according to the invention include vascular catheters, peritoneal catheters, electrodes, shunts, drainages, permanent venous cannulas, cannulas used for drawing blood, ports, and pins (wires of a fixture projecting to the outside). Also included are here tubular shaft instruments, such as endoscopes and trocars, which penetrate the skin, such as for example for arthroscopy, laparoscopy, and other surgical procedures. Medical instruments particularly not included in this term are those not penetrating the skin, such as bladder catheters, gastroscopes, coloscopes, and bronchoscopes, for example.

Catheters are flexible or stiff hollow capillaries with one or more lumina, comprising at least one inlet and outlet, optionally with an inlet at the distal end, i.e. facing away from the body. Vascular catheters include all catheters common in medicine, such as those for the application of liquid substances, for draining fluids, such as blood, or for gases (e.g., shunts), as well as cardiac catheters, permanent venous catheters, e.g., for V. jugularis or V. subclavia.

The composition is applied like a film onto the catheter. Here, the viscosity of the composition is selected such that it can cover it as a film (continuous film or film (almost) completely covering the surface), adhering to the instrument particularly in the moist state. The thickness of the layer applied on the catheter may range from 10 µm to 500 µm; however, it may also be thicker. At a layer thickness starting at 10 µm, a sufficient quantity of anti-infectious compound is applied in order to yield the anti-infectious effect. The thickness of the layer preferably stays below 3 mm; below 2 mm is even more preferable. Preferably, a minimum layer thickness of 0.1 mm is achieved. Here, the coating shall cover at least 80%, preferably at least 90%, further preferred at least 95% or 100% of the surface of the medical instrument, which shall remain in the body.

A viscous composition according to the invention is designed such that at the latest as soon as it is applied on the medical instrument it largely remains in its applied form. The composition is preferably applied like a film or a coating onto the medical instrument. In a preferred embodiment, the viscosity of the composition is such that the composition adheres as a film on the catheter as long as no shearing forces act upon it. This way, the composition can be wiped off.

Such features can be yielded, for example, by mixing a liquid, preferably an aqueous liquid, with a gel former and/or a thixotropic or a thickening agent. Examples for this are bentonite, silicic acids, polyacrylic acids, (PAA, e.g., carbomeres), polyvinyl pyrrolidone, polyvinyl alcohols (PVA), polyacrylate, cellulose, and cellulose derivatives such as hydroxyl ethyl cellulose, Na-carboxyl methyl cellulose, hydroxyl propyl methyl cellulose, hydroxyl ethyl cellulose, xanthan gum, hypromellose, gelatin, pectin, casein, agar-agar, starch, tragacanth, polyethylene glycol, natural or synthetic albumins, as well as their mixtures, hyaluronic acid, polyethylene glycol, lecithin, glycerin, glucose, hydroxyl propyl methyl cellulose, propylene glycol, and/or polysorbate 80, dexpanthenol, and polysaccharides (e.g. carrageen). Preferably the gel former is a carbomer. Examples for carbomers include Carbopol ETD2020, 1342, 1382, or Carbomer 974P. Thixotropes include, for example, liquids with a portion of pyogenic silicic acid (in medical qualities with a surface area of 100-600 $m^2$ per g). In a preferred embodiment the gel former is tolerated by the human organism without any complications. It is even more preferable if it is free of cellulose or cellulose derivatives.

Due to these features of the composition, it is also not washed off until the medical instrument is used and/or when an applicator is used to apply it upon the medical instrument.

Typically the composition comprises the gel former in quantities from 0.01 to 20% by weight, particularly 0.1 to 10% by weight, preferably 0.2 to 5% by weight, particularly preferred 0.3 to 2% by weight, each in reference to the composition. In the event the gel former is PVA, the ratio of PVA in the composition ranges from 0.1 to 20% by weight, preferably from 2 to 10% by weight, e.g., amounts to 3, 4, 5, 6, 7, 8, or 9%. A rate of 5% by weight is particularly preferred. If the gel former is PAA, e.g., a carbomer, typical concentrations of gel formers range from 0.1 to 2% by weight, preferably 0.2 to 1.5% by weight, e.g., amounting to 0.3, 0.4, 0.5, 0.6, 0.7, 0.8, 0.9, 1.0, 1.1, 1.2, 1.3, or 1.4% by weight. Particularly preferred is a range from 0.5 to 0.7% by weight.

In general, the composition shows a physiologically tolerated pH-value. This includes pH-values ranging from 4 to 8, preferably 5 to 8, particularly preferred 5 to 7. Furthermore, within the scope of the present invention, it may be provided that the composition additionally includes at least one acid and/or base, particularly for adjusting the pH-value, preferably for adjusting a physiologically tolerated pH-value, preferably in order to form a buffer system. The respective buffer systems are well known to one trained in the art, so that no additional explanations are necessary regarding this.

The composition according to the invention includes at least one anti-infectious compound.

The term "anti-infectious" describes an at least inactivating effect of a compound upon microorganisms. Preferably, anti-infectious compounds show only negligible side effects in their effective dosage, particularly when brought into contact with blood or blood vessels; however, they may also be toxic for body cells within a certain tolerable range, such as for example in case of ethanol. Anti-infectious compounds or compositions are sufficiently known in prior art.

In general, all anti-infectious compounds are suitable for an application in the present invention which show a high degree of tolerance by the body. Furthermore, at least one anti-infectious compound is provided in a concentration ensuring its anti-infectious effectiveness.

In a preferred embodiment the anti-infectious composition is selected from chlorhexidine and octenidine or a combination thereof.

If the composition comprises octenidine (1,1'-(1.1 O-decandiyl) to [4-(octylamino)pyridinium]-dichloride and/or 1,1'-decamethylene[(1,4-dihydro-4-octylimino)pyridinium] dichloride $C_{36}H_{64}N_3Cl_2$) and/or its salts, particularly octenidine di-hydrochloride, they are commonly included in quantities from 0.01 to 2% by weight, particularly 0.02 to 1% by weight, preferably 0.03 to 0.5% by weight, even more preferably from 0.03 to 0.12%, for example amounting to 0.05, 0.06, 0.07, 0.08, 0.09, 0.1, 0.11, 0.12%, each in reference to the compositions included.

It has surprisingly shown that, contrary to the common concentration of 0.1%, a concentration of 0.05% octenidine is also of sufficiently good effectiveness and additional has the advantage of lower irritation. Without agreeing to a predetermined effective mechanism, the inventors assume that the reason is given in a lower distribution volume in a gel formulation in reference to the overall quantity of the gel.

Another preferred embodiment of the anti-infectious composition additionally includes also 2-phenoxy ethanol in a quantity from 0.5 to 4%, preferably 2%.

Chlorhexidine may be present in quantities from 0.1 to 5%, preferably from 0.5 to 2%, e.g., amounting to 1% or 1.5%. A preferred anti-infectious composition includes chlorhexidine gluconate as an anti-infectious compound, which typically is applied in a concentration from 0.1 to 5%, preferably from 0.5 to 2%, e.g., 1% or 1.5%.

In another preferred embodiment, the anti-infectious compound is selected from quaternary ammonium compounds, such as cetylpyridinium chloride (concentration between 0.01 to 0.05%, preferably 0.03%, it may also be present together with 0.1% hexetidine), cetylpyridinium bromide, cetyltrimethyl ammonium bromide, or benzalconium chloride (concentration preferably from 0.05% to 0.5%), 2-phenoxy ethanol, triclosan, ethyl alcohol, isopropanol, polyhexanide, (preferably 0.01 to 20%, more preferably 0.05 to 0.5%, more preferably in combination with approximately equal concentrations of undecylene amidopropyl betaine) macrogolum or a combination thereof. In another embodiment the above compounds are present in addition to octenidine or chlorhexidine.

In another preferred embodiment the anti-infectious compound is selected from bacitracin, gramicidin, polymyxin B, neomycin, fusidinic acid, gentamycin, erythromycin, chloramphenicol, tetracycline (minocycline, doxycycline) or a gyrase inhibitor (levofloxacin, ciprofloxacin), rifampin, rifampicin, lincosamide, trimethoprim/sulfamethoxacol [sic: sulfamethoxazol], vancomycin, linezolid, mupirocin, or a combination thereof. These effective agents are commonly present in a quantity of up to 2% by weight. In another preferred embodiment the above-stated compounds are present in addition to octenidine or chlorhexidine.

In another preferred embodiment the composition additionally includes an anti-infectious compound selected from povidone-iodine and phenoxy ethanol or a combination thereof.

Common concentrations of polyvinyl pyrrolidone-iodine=povidone-iodine=PVP-I are 4 to 12%, particularly 5%. Particularly preferred anti-infectious compounds or mixtures thereof comprise octenidine hydrochloride from 0.03 to 0.12% alone or with 2 to 4% phenoxy ethanol, 0.5 to 5% chlorhexidine, also as a chlorhexidine digluconate, gyrase inhibitors, such as ofloxacin or staphylococci-specific antibiotics, such as fusdic acid, rifampin, and others.

The anti-infectious compounds can also be present as and/or in liposomes, which offers advantages for the hydrophobic surfaces and in case of incompatible mixtures.

The method according to the invention leads to a reduction of the number of cases of sepsis caused by inserting medical instruments into blood vessels, particularly catheter sepsis. The term "sepsis caused by medical instruments" relates to septic infections in context with the insertion of foreign materials into the body for medical purposes (using medical instruments). This particularly applies for medical instruments remaining in the body of the patient over several replication cycles of pathogens, such as staphylococci, so that a biofilm and a dangerous primarily hematogenic sepsis associated with a foreign object can develop. By the method according to the invention, not only the number of sepsis-related fatalities is reduced, but also the admission days in the intensive care unit due to sepsis. The relief of burden on the physicians, clinics, and the health care system in general should not be disregarded, either. Without being limited to a certain scientific theory, the inventors assume that these results are achieved based on three effects connected to the method according to the invention.

Infectious germs from deeper skin layers, which normally are out of the reach of surface disinfectants, usually adhere to the catheter upon penetration of the skin. Due to the antiseptic film on the catheter they are now entrained to a lesser degree and additionally inactivated by the antiseptic effect.

Inactivation of germs collecting on the catheter directly after removal thereof, for example from the air via airborne infection or contact with unsterile surfaces Washing effect: Achieving a washing effect on the medical instrument by applying a composition according to the invention like a film on the medical instrument which is pushed off the catheter during the insertion through the skin, so that at the insertion site germs are transferred through the skin from the medical instrument into the composition and the quantity of the pushed-off gel increases at the insertion site during the penetration through the skin.

In other words, due to the viscosity of the composition, it is achieved that on the one hand it remains on the medical instrument prior to insertion into a blood vessel. On the other hand the applied film is reduced during the insertion into the blood vessel by the skin ("pushed off") and equalized, because the medical instrument e.g., a catheter, is pushed through the drop of composition developing on the skin at the insertion site. In addition to the application, this has another "washing effect." However, the composition is effective in the insertion channel, because small amounts of the composition are inserted into the skin and thus into the epidermis and are partially effective in the dermis, and ultimately they are retained by the fibrous collagen bundles of the dermis. Germs are usually located in these areas, which are entrained by the medical instrument during the insertion. This way, the method according to the invention yields an additional disinfection of the insertion channel.

The method according to the invention can also be used for drawing blood. Blood cultures show false positive results in approximately 10% of all cases. This leads to considerable costs and the delay of urgently needed diagnoses. With the present method, cannulas intended for taking blood samples for the purpose of growing blood cultures can advantageously be prevented from contamination with germs in order to thereby lower the rate of false positive cultures.

In one preferred embodiment the composition is present in the form of a gel.

Within the scope of the present invention, the term "gel" shall be understood particularly as gelatinized liquids, which can be produced with the help of suitable gelling agents, also called gel formers. This preferably represents finely dispersed systems with at least one solid and one liquid phase, with the gelling agent and/or the gel former representing the solid phase. Within the scope of the present invention, the liquid phase as well as solutions shall also include dispersions, with the dispersions in turn may be present as solid-liquid dispersions. The gel formers cause a network to develop in the finely dispersed system, forming a gel and influencing the viscosity of the mixture, which can frequently be observed as "gelatinization" and/or "thickening". Gels may be described as viscous-elastic fluids, i.e. the fluid features of a gel are here between those of an ideal liquid and those of an ideal solid body. The gels to be used within the scope of the invention can neither be torn nor cut.

Particularly effective gelatinous or thickened substance and/or features are yielded when the composition according to the invention shows a Brookfield-viscosity from 10-100 (Brookfield, cP×1,000, 20 rpm) or 1 cP=1 mPa·s=0.001 Pa·s is the dynamic viscosity 10,000-100,000 mPas. In a preferred embodiment, the composition shows a dynamic viscosity η (mPa·s) greater than 1, preferably η (mPa·s) greater than 4, even more preferably greater than 5, and most preferred greater than 20. The viscosity is preferably lower than 100 Pa·s. A preferred range for gels, e.g., PAA gels, particularly those with EDT 2020, amounts from 20 to 60 Pa·s.

The composition according to the invention may additionally include a colorant for an optic control of the application.

Furthermore, stabilizers, e.g., those acting stabilizing upon the gel foundation or at least the anti-infectious compound, such as EDTA (ethylene diamine tetra-acetic acid), ethylene glycol-bis(amino ethyl ether)-N,N'-tetra-acetic acid (EGTA), sodium gluconate, or other ones may be added in concentrations from 0.0001 to 1% by weight. Here, tensides, such as polysorbate, triton, tween, or others may also be present in concentrations from 0.0001 to 0.1%. They increase the wettability of hydrophobic surfaces.

Furthermore, preservatives may be added to the composition, such as methyl-4-hydroxy benzoate, propyl-4-hydroxy benzoate.

Furthermore, within the scope of the present invention, it may be provided that the composition according to the invention includes additionally a preferably polyvalent alcohol. The polyvalent alcohol serves on the one hand as a moisturizer and supports the adjustment of optimal viscosity features of the composition according to the invention and acts on the other hand as a carrier substance, which further increases the stability of the compositions according to the invention. Exemplary polyols according to the invention are selected from diols, triols, and tetraols, e.g., mannitol or sorbitol.

Within the scope of the present invention, it is advantageous for the preferably polyvalent alcohol to be selected from the group of polyvinyl alcohols, glycerin, glycols, and (poly)alkylene glycols, as well as their combinations and mixtures, preferably alkylene or polyalkylene glycols, particularly preferred propylene glycol.

When the composition according to the invention includes a preferably polyvalent alcohol, this preferably polyvalent alcohol may be present in the composition in a quantity from 10 to 80% by weight, particularly from 15 to 70% by weight, preferably 20 to 60% by weight, each in reference to the composition.

Furthermore, the composition according to the invention generally also includes water, particularly in quantities of at least 10% by weight, particularly at least 20% by weight, preferably at least 30% by weight, each in reference to the composition.

In this context it is preferred for the composition to include the water in quantities from 10 to 99% by weight, particularly 80 to 85% by weight, particularly preferred 80 to 99.5% by weight, each in reference to the composition.

Particularly stable and easily applicable compositions are yielded when the composition according to the invention comprises a mixture or a blend of at least one preferably polyvalent alcohol and water. Preferably the ratio of water, each in reference to the mixture or the blend, shows at least 10% by weight, particularly at least 30% by weight, preferably at least 50% by weight. Furthermore, it is particularly preferred according to the invention that the ratio by weight of water to alcohol in the composition ranges from 9:1 to 1:5, particularly from 3:1 to 1:3, preferably from 2:1 to 1:2, particularly preferred from 1.5:1 to 1:1.5.

As an alternative to the above embodiments, e.g., a gel, the preferably viscous composition may represent a non-aqueous, biocompatible fat or oil (e.g., soybean oil, olive oil) and particularly their mixtures (emulsions) with water fulfilling the above criteria.

The composition may also be foam-like. For this purpose it comprises at least one compound which promotes the frothing of the composition under suitable conditions (see below). Suitable foaming agents are, e.g., compounds, included alone or in combination with other surface-active compounds, such as detergents (tensides) (polysorbate, triton, tween, concentrations 1-0.1%) or also proteins such as natural or synthetic albumin (concentrations 0.1-50%) and/or polyvinyl alcohol with an aqueous solvent, which additionally includes a foaming agent. This may represent dissolved or chemically bonded carbon dioxide, nitrogen, or butane.

Furthermore, such an addition without a foaming agent can generate a liquid foam, with the additive being present in an open-pored, flexible foamed solid (e.g., polyurethane), by which air is mixed into the liquid during repeated compression with foam developing. PVA-gels in particular can be foamed especially easily.

In a preferred embodiment, the anti-infectious composition is applied via an applicator. In a particularly preferred embodiment, the applicator may represent the applicator according to the invention described in the following.

The applicator is preferably a sterile single-use medical product; however, it may also be present in a reusable form if its components are made from a material that can be disinfected and/or sterilized.

In a preferred embodiment the composition is present as a polyacrylic acidic gel, preferably as carbomer gel, with the polyacrylic acid ratio preferably ranging from 0.1 to 2% by weight, e.g., amounting to 0.4, 0.5, 0.6, 0.7, 0.8, 1, 1.5% by weight.

The term carbomer is a general term for homopolymer polyacrylic acids (PAA). A carbomer is commonly available as a white powder in various molecular sizes and is used for example as an emulsion stabilizer or thickening agent. Examples are Carbomer 940, 947, 943, or also Carbopol (trademark of Lubrizol).

The additional use of polyvinyl pyrrolidone (PVP) has proven advantageous due to better stability (i.e. consistent layer in spite of influencing forces, such as gravity or hydrophilic/hydrophobic interactions) of the film on hydrophobic surfaces and due to the surprisingly much improved ability to mix octenidine or chlorhexidine into compositions, which represent gels for example. For this purpose, the octenidine and/or chlorhexidine is first dissolved in PVP and then mixed with the gel. The PVP portion may range from 0.1 to 6%. Thus, in another preferred embodiment the composition also comprises polyvinyl pyrrolidone at a range from 0.1 to 6% by weight, preferably 0.1 to 5% by weight, more preferably from 0.5 to 5% by weight, more preferably from 1 to 3% by weight, amounting e.g. to 2.1, 2.2, 2.3, 2.4, or 2.5% by weight. In a preferred embodiment, the composition is present as a PAA gel, preferably carbomer gel, and shows polyvinyl pyrrolidone, in the above-mentioned concentrations for example.

PVP is a water-soluble polymer of the monomer N-vinyl pyrrolidone and is additionally known as povidone, Polyvidone. Povidone is usually listed with its molecular size, e.g., povidone K90, K30, K25; additionally, it is otherwise commercially available as Kollidon® (BASF), Plasdone® (ISP).

In a particularly preferred embodiment, the composition comprises PAA, e.g. carbomer or PVA as a gel former, PVP as well as octenidine and/or chlorhexidine, all of them in the concentration ranges listed on other pages.

In another particularly preferred embodiment the composition comprises from 0.2 to 1% carbomer and from 0.01 to 0.12 octenidine, e.g. 0.03-0.07% carbomer, e.g. Carbopol ETD 2020 NF, and 0.04-0.1% octenidine, as well as 0.5-5% polyvinyl pyrrolidone K90 (M 360 000 g/mol).

In another preferred embodiment, the medical instrument is intended to be inserted into an invasively generated body opening for an extended stay inside the body. The expression "extended stay" includes periods from 0.5 days to 3 months, typically 3-28 days, for example 8 to 12 days, as frequently used in patients in the intensive care unit, for example.

Furthermore, the present invention relates to at least one composition comprising an anti-infectious compound, characterized in that the composition is embodied in order to adhere like a film on the medical instrument after being brought into contact with the medical instrument to be inserted perioperatively into an invasively generated body opening and that at least a portion of the composition, which adheres like a film, is transferred into the body at least to the epidermis during the insertion of the medical instrument.

In another embodiment, the present invention relates to the use of a composition as described above for the perioperative disinfection of medical instruments to be inserted into invasively generated body openings, particularly vascular catheters or endoscopes, for washing the above-mentioned medical instruments, or as an anti-adhesive or a lubricant on the above-mentioned medical instruments, or for disinfecting an insertion channel generated by the insertion of a medical instrument into the body.

In another embodiment, the present invention relates to a medical instrument to be inserted into an invasively generated body opening, particularly into blood vessels, with preferably a viscous or foam-like anti-infectious composition comprising a compound, preferably selected from chlorhexidine and octenidine, adhering on the medical instrument, characterized in that the composition is embodied in order to adhere on the medical instrument like a film after being brought into contact therewith, and that the film-like adhesive composition reaches at least the epidermis upon insertion of the medical instrument into the body.

Furthermore, the invention relates to a method for the production of at least one composition comprising an anti-infectious compound for the perioperative disinfection of a medical instrument to be inserted into an invasively generated body opening, or for the disinfection of an insertion channel generated by inserting a medical instrument into the body, comprising (a) the production of a gel, preferably a PPA, more preferably carbomer, or PVA gel in $H_2O$ with a pH ranging from 5 to 8, (b) a solution of an anti-infectious substance selected from octenidine and chlorhexidine in polyvinyl pyrrolidone, and (c) the mixing of the gel from (a) with the solution of (b) such that the gel is present in the gel at a range from 0.1 to 20% by weight, e.g. PAA at a range from 0.1 and 2% by weight, or PVA at a range from 0.1 to 20% by weight, the anti-infectious substance in a concentration from 0.01 to 2% by weight, and the polyvinyl pyrrolidone in a concentration from 0.1 to 5%.

The production of PAA and PVA gels is known in prior art. In general, the desired quantity of substance is added to water and left standing for swelling. Common swelling times range from 30 min to 2 hours.

Colorants or preservatives, nourishment, stabilizers, or moisturizers are possible additional substances included here and well known in prior art.

An applicator for the perioperative disinfection of a medical instrument, which can and/or shall be inserted into an invasively generated body opening, is also an objective of the present invention, with the applicator being embodied such that a viscous or foam-like composition, comprising at least one anti-infectious compound, can be applied by a relative motion between the applicator and the medical instrument upon the surface of the medical instrument, characterized in that the applicator comprises a retention device for an anti-infectious composition, with the applicator showing a hollow embodied reservoir with a conically tapering section, preferably located in the rear in the direction of motion.

The retention device is located, in a preferred embodiment, in the rear of the applicator in the direction of motion. In another preferred embodiment, the conically tapering section is located horizontally on the applicator in the rear in the direction of motion.

Unless stipulated otherwise, the parameters and features described for the above embodiment can also be applied to all other embodiments disclosed here. This particularly applies to the anti-infectious composition to be used with the applicator.

In a preferred embodiment the conically tapering section of the applicator represents the retention device.

Via the retention device, the retention of excess gel is achieved. Additionally, it allows the application through gel penetration openings and the application is rendered largely homogenous.

In another preferred embodiment, a further retention device may also be provided at the front end of the applicator, seen in the direction of motion. It may be embodied, e.g., in the form of a preferably elastically embodied diaphragm, closing said end, e.g., made from plastic or metal in the form of a film. An opening is located in the retention device for the penetration of the applicator.

In another preferred embodiment, the conically tapering section shows a multitude of slots, preferably embodied starting at the rear end of the conical section, seen in the direction of motion, and extending in the axial direction. If the applicator shows a conically tapering section, no more than one of the slots is continuous, in order to ensure that the applicator is provided in one piece.

In another preferred embodiment the conically tapering section shows essentially a frustum shape. In other words, no conical tip is provided; however, the conically tapering section is still embodied such that on its end, i.e. in the proximity of a cover area of the frustum, it is closed such that the composition comprising at least one anti-infectious compound cannot independently discharge from the applicator, i.e. without any external influence.

Frustum-shaped conically tapering sections may show openings located at the rear, seen in the direction of motion, which are embodied such that at least one composition comprising at least one anti-infectious compound cannot independently discharge from the applicator, i.e. without any external influence. The diameter of such an opening may range, e.g., from 0.5 to 4 mm, e.g., amounting to approximately 0.8, approximately 0.9, approximately 1, approximately 1.1, approximately 1.2, approximately 1.3, e.g., 1.35, approximately 1.4, approximately 1 or approximately 1.6 mm.

In an alternative embodiment, the conically tapering section is essentially cone-shaped, i.e. shows a tip. This tip is preferably not closed but embodied such that the medical instrument, when penetrating the applicator, can exit at said tip. If the tip is closed, however, it is embodied such that the medical instrument can easily pierce it by the applicator being guided through it. If it is not necessary for the medical instrument to be guided through by the applicator, but rather it is pushed into it and then pulled back out, the tip shall be designed such that a brief pressure applied by an accidental impact of the medical instrument upon the tip leads to no negative consequences for the applicator.

In the context with the shape of a conically tapering section, the term "essentially" relates to a tendency for tapering a roundish basic form towards the rear, seen in the direction of motion. In other words, the jacket shape of the cone and/or the frustum may also taper unevenly, e.g., arched or wavy.

In another preferred embodiment, the applicator comprises two conically tapering sections arranged behind each other and showing different angles α, with the angle of the conically tapering section located in the front in the direction of motion being smaller than the one of the conically tapering section located at the end in the direction of motion.

The applicator may show a first part which is contacted manually and a second one which acts as a carrier or reservoir for the composition.

Here, the carrier or the reservoir is fastened at the first part. The applicator may also be designed only comprising the carrier or the reservoir, which then itself is contacted by the hand. Part, carrier, or hand may partially or entirely also be referred to in their plural form.

The applicator comprises at least one reservoir for the anti-infectious composition, e.g., in an interior zone. The reservoir is designed such that it allows supplying the parts of the applicator which come into contact with the medical instrument with the above-mentioned composition, so that a largely homogenous application is ensured on the medical instrument.

The applicator is embodied such that the composition can be applied upon the medical instrument e.g., a catheter by pushing or pulling or both by pushing as well as pulling the medical instrument through the applicator, so that the composition is applied upon the medical instrument in layers or like a film.

The carrier and/or the reservoir may be embodied as an open-pored foam, a pressurized sterile container, or at least partially a flexible container or a blister that can be crushed. In case of a pressurized container, the composition can be released via a valve or by a pin piercing it. In a preferred embodiment, the composition then foams by the presence of dissolved $CO_2$ or $N_2$.

The carrier may also be present as a reservoir for the anti-infectious composition, which comprises the composition, which in case of sufficient viscosity and/or sufficiently stable foam remains at the intended place.

The applicator shows a retention device for the anti-infectious composition, preferably in the direction of motion of the medical instrument. The preferred embodiment, in which the retention device is located in the direction of motion of the medical instrument, is equivalent to an arrangement at the rear end of the applicator in reference to the relative direction of motion. Such a retention device prevents the discharge of the anti-infectious composition beyond the desired application upon the medical instrument, e.g., in the form of seepage or dripping.

The retention device may be made from plastic, for example as an elastic film, preferably showing a central opening for the medical instrument. The retention device may show slots at suitable positions, so that the present applicator can be used for medical instruments with different diameters.

In a preferred embodiment, the retention device shows at least one opening. The opening may e.g. be located at a cover area of the essentially frustum-shaped, conically tapering section, which in this embodiment comprises the retention device. This embodiment is particularly suited for applicators through which a medical instrument is guided. In this case the opening serves as the outlet for the medical instrument.

Alternatively, the retention device may show at least one opening at an arbitrary location. Such openings can allow excess composition to be discharged when a medical instrument is inserted into an applicator and is pulled back out of it.

In another preferred embodiment, at least one opening is additionally slotted. For example, the applicator may laterally show a slot, continuous in the axial direction. This may serve as the inlet and/or outlet for the medical instrument. Here, the [insertion of the] medical instrument may occur by moving apart the edges generated at the applicator by the slot. The moving apart may occur either by the use of an elastic material for the applicator or by a link at another point extending in the axial direction. The continuous slot allows different procedures for the application of an anti-infectious substance upon the medical instrument.

After insertion of the medical instrument via the continuous slot, the applicator, previously filled with gel, is closed, with it being able to be arranged at an arbitrary position along the medical instrument, and is pulled off towards its free end, resulting in the coating. Alternatively, inversely the medical instrument may also be inserted into the applicator via the front end of the applicator, seen in the direction of motion, and then after coating being removed again by opening the applicator at the continuous slot.

Depending on the source and location of the anti-infectious composition on the applicator, the composition can be applied on the medical instrument by way of moving said medical instrument (e.g., pulling or pushing) during the presence of the medical instrument on site. Accordingly, the medical instrument can also be fixed and guided with said applicator such that it no longer needs to be touched with gloved hands. Alternatively, an applicator can also be used with two relative motions and then no longer needs to show a continuous slot. Here, the catheter is first inserted with its free end at the end of the applicator located in the front, seen in the direction of motion, and then pulled out again.

In other embodiments, the applicator is not provided with a continuous slot. In these embodiments, the conically tapering section may include a number of slots, which are not continuous, however.

In particular embodiments, the conically tapering section shows several slots, so that the slots preferably extend in a stellar fashion and form a rosette-like structure. The opening is preferably arranged in the center of the converging slots, forming a rosette together with these slots. By the multitude of slots and a suitable material strength the applicator is preferably elastic in the conically tapering section. The slots are preferably embodied extending in the axial direction, starting at the end of the conical section located in the rear, seen in the direction of motion. More preferably, the slots form a multitude of flexible tongues, acting as stripping elements and/or as retention elements. Preferably, the material of this part of the applicator is selected such that, when the medical instrument is guided through the applicator, the tongues cling to said applicator so that the film of anti-infectious composition applied in the applicator essentially remains intact. The thickness of the tongues also needs to be adjusted to these conditions. Accordingly, the material of the tongues is preferably provided in an elastic form and shows a wall thickness (thickness from the outside towards the inside) from approximately 0.2 to 1.2 mm, preferably from 0.3 to 0.8 mm. The number of tongues commonly ranges from 3 to 20, preferably from 5 to 10, e.g., amounting to 6, 7, 8, or 9.

The applicator may be prefilled with the gel. The gel contacting the catheter is pulled out of the applicator by a relative motion of said applicator and partially retained by the tongues (stored), but carried towards the outside through the slots with a film or layer remaining on the catheter.

In one preferred embodiment, a cylindrical section follows the conical section in the direction of motion. This cylindrical section may be open at its front end in the direction of motion. Alternatively, the cylindrical section is closed at the front end in the direction of motion and shows only one opening which is suitable to serve as an inlet for the medical instrument into the applicator. In such an embodiment, an elastic film may cover this very end, showing a suitable opening.

Like the conically tapering section, the cylindrical section may be embodied as a reservoir for the anti-infectious composition.

Although the conically tapering section ensures coating of the medical instrument, the cylindrical section can optimize said coating, particularly with regards to applying the film over the entire length of the medical instrument in case of longer instruments.

In another preferred embodiment, the applicator is provided with an insertion aid for the medical instrument, preferably at the lateral slot extending continuously in the axial direction. For example, the insertion aid may be embodied such that the edges of the continuous slot are bent outwardly like lips, at least partially, and are continued. Alternatively, the insertion aid may also be embodied as an expansion of the continuous slot which is located at the front at the applicator, seen in the direction of motion.

In order to prevent any discharge of the anti-infectious composition in the area of the continuous slot, at least one sealing edge, preferably two opposite sealing edges may be provided in this area. The sealing edges may be arranged and constrict the continuous slot such that any discharge of the anti-infectious composition is prevented e.g., due to surface tension. In doing so, the sealing edges may approach, for example, the flanks of the continuous slot; however, they may also be embodied contacting or overlapping each other.

The applicator may be prefilled or pre-coated with the composition. Such an arrangement may be provided sterilized in a package and is only removed from the package shortly before applying it on the medical instrument.

The applicator may show at its exterior at least two engagement zones, which preferably are sized such that a human thumb or finger fits into them. The engagement zones may be formed from plastic or an elastomer, into which one thumb and index finger, respectively, can be inserted. The engagement zones may be embodied cylindrically or bag-like, for example. The engagement zones may be connected to each other at the proximal side.

In order to facilitate the motion of the applicator along the medical instrument, a pulling aid may be provided at the front, seen in the direction of motion. This pulling aid may be formed, for example, such that wing-like projections are arranged at the end of the applicator essentially facing away from each other in the radial direction, which on the one hand prevent any slippage in this direction and on the other hand also serve as contact points for pulling the applicator. Alternatively, a circumferential collar may also be provided at the end as a pulling aid, which also prevents slippage and facilitates pulling. The circumferential collar may also be embodied slotted, so that a lateral insertion of the medical instrument and/or a removal of the applicator from a medical instrument are still possible. In particular embodiments the tension aid is shaped such that it forms engagement zones.

Both the wing-like projections as well as the circumferential collar may show reinforcing ribs for stabilization in the tensile direction, which can reduce or prevent any kinking or bending in the tensile direction.

The engagement zones may be characterized by a suitable surface structure, for example striations or ribs or nubs extending in the lateral direction. Such surface structuring can simultaneously improve the feel of the surface and prevent the user from slipping.

The ribs may be embodied in the form of arrow tips, i.e. showing two approaching flanks. This way these ribs can simultaneously also indicate the tensile direction of the applicator.

The applicator preferably represents a sterile and/or sterilized single-use medical product or one that can be sterilized and reused.

The applicator may show an application zone and/or internal zone in which the medical instrument comes into contact with the composition. Preferably, it also shows a distribution zone via which the coating is equalized so that excess composition is retained. Furthermore, the applicator according to the invention shows a handling zone with which the applicator can be manually guided.

The applicator may comprise a soft, flexible, and also elastic material, e.g., silicon rubber, elastomer, thermoplast, or a foamed material. The applicator according to the invention is a one-piece, sterile product, preferably a single-use product, which is removed from the package after opening. The sterile anti-infectious composition may also be applied as late as during the use of the applicator or filled into it, for example from a syringe or another (single-use) container. The applicator, the quantity of the composition, and the method used shall ensure that no more of the composition than absolutely necessary for achieving the desired effect reaches the lumen/lumina of the medical instrument.

The dimensions of an applicator according to the invention depend on the medical instrument to be used with it. Commonly the applicator shows a length from 30 mm to 80 mm, preferably from 40 to 70 mm. Particularly preferred embodiments show a length from 45 to 65 mm.

The length of the individual sections of the applicator, e.g., at least one conically tapering section or a cylindrical section, also depend on the requirements of the medical instrument to be inserted. A conically tapering section located in the rear in the direction of motion may show, e.g., a length from 5 to 20 mm; a section following in the direction of motion in front of a cylindrical section is commonly longer than the conically tapering section located at the end in the direction of motion, and shows a length, e.g., from 20 to 60 mm, preferably from 25 to 45 mm, e.g., amounting to 30, 35, or 40 mm.

The diameter of an applicator according to the invention ranges commonly from 8 to 30 mm, preferably from 10 to 20 mm. For example, an applicator shows a diameter of 12, 14, 15, or 17 mm without including any potentially present insertion aids in the dimension.

The length of the slots located in the conically tapering section preferably falls short of the length of the conically tapering section itself; however, in individual cases the slots may also be extended in the following conically tapering or cylindrical section as long as they are not extending over the entire length of the applicator.

Furthermore, the invention includes a kit comprising the applicator described in the present application as well as one or more of the above-described compositions. The applicator, including the already filled-in composition, may also be provided in a packaging. This packaging is preferably a contoured packaging, e.g., a blister package, which provides an opening mechanism at the front end, seen in the direction of motion of the applicator. In one embodiment, the kit may additionally include a medical instrument, preferably a vascular catheter or another above-described medical instrument. The packaging protects the applicator from contaminants, keeps it sterile, and additionally prevents the gel from drying out.

In one embodiment, the applicator may be opened at any arbitrary point of the medical instrument and be removed from said medical instrument without the applicator being pulled completely over the medical instrument.

The applicator may comprise an elastic material, which can be produced e.g., by way of foaming or injection molding.

In one embodiment the applicator may comprise open-pored foam and is essentially cylindrical, for example. This cylinder may comprise the preferably viscous composition and is slotted longitudinally to its middle. For example, prior to use such an applicator can be located in a film, which is open longitudinally or can be opened via a predetermined breaking point.

One or both ends of the applicator may be closed by an elastomer or film disk, comprising a central hole in the middle as well as a notch from the hole to the edge so that the applicator can be placed over the catheter and compressed, and when pulling the catheter through it excess composition is retained, and a thin film remains on the medical instrument due to the elastic feature of the disk.

Further, the present invention relates to the use of an applicator according to the invention for applying a preferably viscous composition, comprising at least one anti-infectious compound, upon a medical instrument to be inserted into blood vessels prior to use of said medical instrument. In a preferred embodiment the composition comprising at least one anti-infectious compound represents the composition according to the invention.

DETAILED DESCRIPTION OF THE DRAWINGS

FIG. 1 shows a side view of an exemplary embodiment in which the antiseptic composition is included in the interior zone 3. Additionally, slotted disks 7 may be provided as retention devices. In order to wipe excess composition off the medical instrument the disks 7 show an opening 9 smaller than the diameter of the medical instrument. The disks 7 may be made from an elastic film material.

The medical instrument may here be pushed through the opening 9, with the slots of the disks 7 providing the option to push in the applicator at any arbitrary point of the catheter and/or pull it off without being forced to pull off the applicator in the opposite direction for removal off the catheter. This is particularly advantageous when only a part of the medical instrument is to be inserted into the body and thus only a partial treatment is required.

The applicator may be made completely from a foamed or molded elastic material and also be produced without a continuous slot.

Figure 2A:
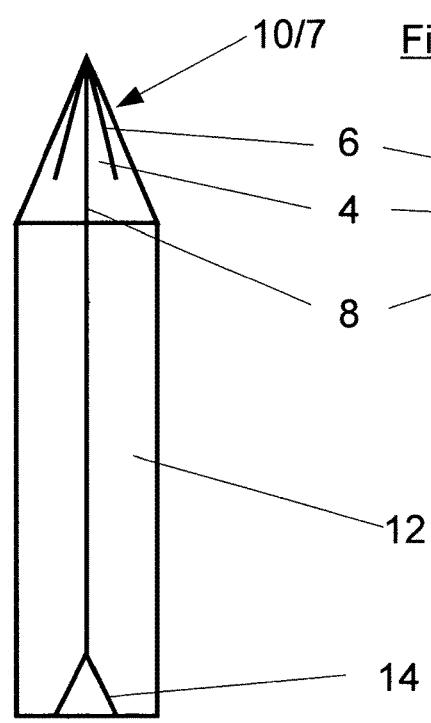
FIG. 2 is a line drawing evidencing an illustration of a first exemplary embodiment in a. a side view and b. a top view of the conically tapering section
Figure 2B:
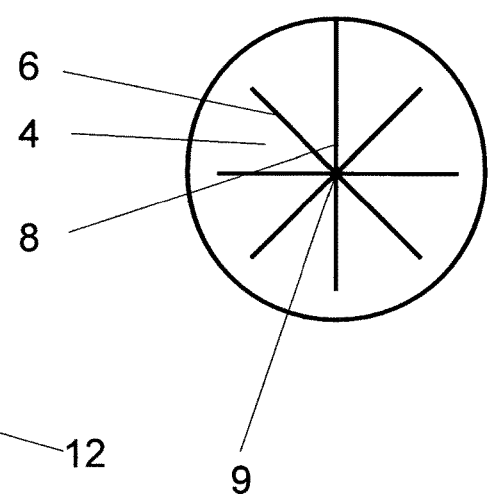

FIG. 2 shows a side view of a second exemplary embodiment of an applicator 30. The applicator 30 is essentially formed from a section 12, essentially embodied cylindrically, which forms the primary portion of a reservoir 2, as well as a subsequent essentially conically tapering section 10. The reservoir 2 includes a composition, at least comprising one anti-infectious compound, and is preferably filled with this. In the present exemplary embodiment the conically tapering section 10 is embodied as a retention device 7 and, seen in the top view, provided with a multitude of slots extending in a stellar fashion, starting at a tip with an opening 9. A jacket surface of the conically tapering section 10 is divided by the slots 6 into a multitude of tongues 4. The tongues 4 are flexible due to a suitable selection of the arrangement and number of slots as well as the material used for the conically tapering section, so that the medical instrument to be inserted can pass through them even when the diameter of the medical instrument exceeds the one of the opening 9. The applicator 30 additionally shows a continuous slot 8, which extends from the opening 9 to a front end of the applicator 30, seen in the direction of motion. Seen in the direction of motion, the continuous slot 8 at the front end is provided with an insertion aid 14. In the present exemplary embodiment the insertion aid is embodied as a wedge-shaped expansion of the continuous slot 8. This way it is possible to more easily bring a medical instrument, which shall be used with the applicator 30, with the help of the insertion aid 14, through the continuous slot 8 into the interior of the applicator 30 and then to guide the applicator 30 in the direction of motion over the medical instrument, resulting in a coating with at least one composition comprising an anti-infectious compound.

FIG. 3 shows the exemplary embodiment illustrated in FIG. 2 in use. A medical instrument 16 is positioned in the applicator 30. The tongues 4 at the conically tapering section 10 are spread apart from each other to such an extent that the medical instrument 16 can be guided through the applicator. In doing so, the tongues 4 cling to the medical instrument 16 such that any excess discharge of the composition comprising at least one anti-infectious compound is prevented; however, in spite of this the medical instrument 16 can be coated with said composition.

FIG. 4 shows a perspective illustration of a third exemplary embodiment of an applicator 30. The applicator is essentially made from a cylindrically embodied section 12, forming the primary part of the reservoir 2, as well as a subsequent, conically tapering section 10. The reservoir 2 contains a composition comprising at least one anti-infectious compound and is preferably filled with this. In the present exemplary embodiment the conically tapering section 10 is embodied as a retention device 7, and seen in the top view, provided with a multitude of slots extending in a stellar fashion, starting from a tip with an opening 9. The slots 6 divide a jacket surface of the conically tapering section 10 into a multitude of tongues 4. The tongues 4 are flexible due to a suitable selection of the arrangement and number of slots as well as the material used for the conically tapering section, so that it is possible for the medical instrument to pass them even if the diameter of the medical instrument exceeds the one of the opening 9. Additionally the applicator 30 comprises a continuous slot 8, which extends from the opening 9 to a front end of the applicator 30, seen in the direction of motion. Positioned at the front, seen in the direction of motion, i.e. at the free end of the cylindrical section 12, the applicator is provided with a pulling aid 20, which in the present exemplary embodiment is formed as a circumferential collar. The circumferential collar 20, embodied at the end, is additionally provided with radially extending reinforcement ribs 18, which prevent any bending of the pulling aid 20 in the direction of motion. The continuous slot 8 is provided with an insertion aid 14 at the front end, seen in the direction of motion. In the present exemplary embodiment, the insertion aid is formed as a wedge-shaped expansion of the continuous slot 8, which extends in the free end section of the cylindrical section radially outwardly and forms a wedge-shaped recess in the pulling aid 20. This way it is possible to more easily transfer a medical device, which shall be used with the applicator 30, with the help of the insertion aid 14, through the continuous slot 8 into the interior of the applicator 30 and then to guide the applicator 30 in the direction of motion over the medical instrument, resulting in a coating with the composition comprising at least one anti-infectious compound.

In the present exemplary embodiment, the cylindrical section 12 is provided at its surfaces with ribs extending essentially in the circumferential direction of the applicator, which simplify the handling of the applicator 30, particularly with gloved hands, and prevent slippage when pulling the applicator off in the direction of motion.

Figure 5:
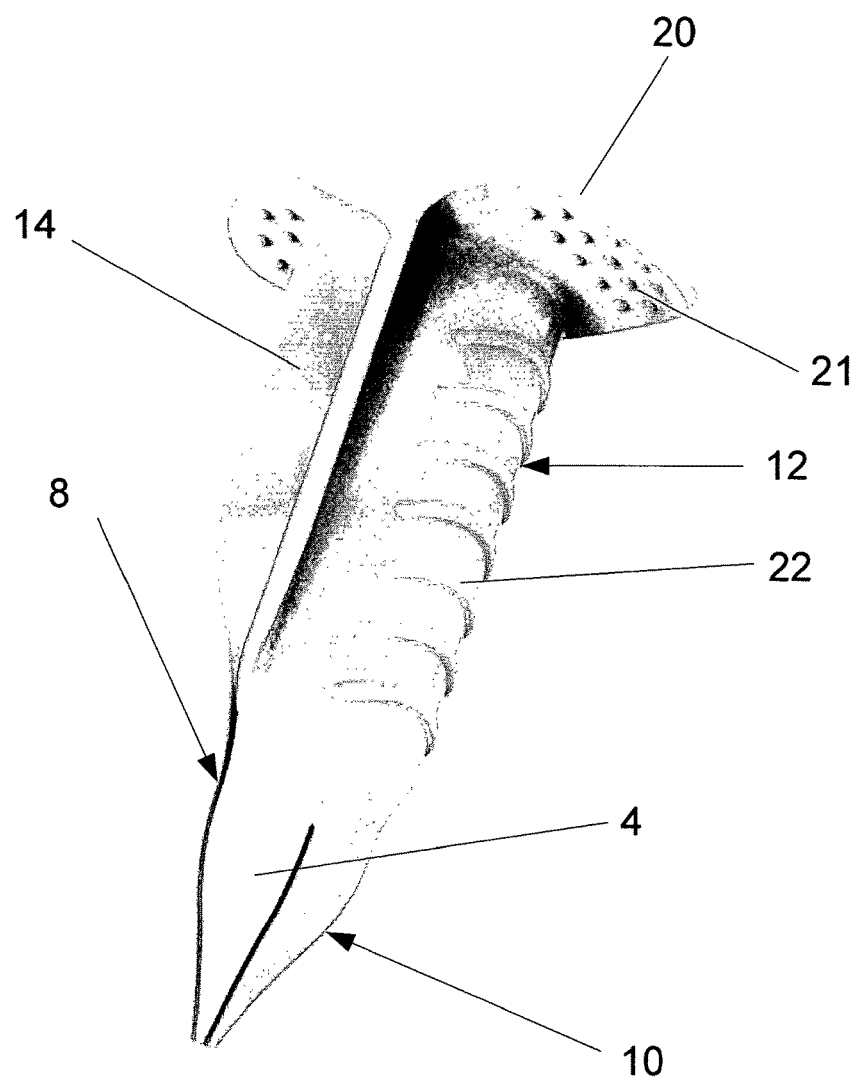
FIG. 5 is a line drawing evidencing a perspective illustration of a third exemplary embodiment

FIG. 5 shows a perspective view of another exemplary embodiment of the applicator 30. The applicator 30 is essentially designed like the applicator 30 of FIG. 4, with the continuous slot 8 being provided with an insertion aid 14 in the area of the entire cylindrical section 12. In the exemplary embodiment shown the insertion aid 14 is formed by an extension of the flanks of the continuous slot 8, extending apart like lips. The lips continue the flanks of the continuous slot 8 essentially in the radial direction and are arranged pointing away from each other, for example at an angle from 20 to 90°. This way they facilitate the insertion of a medical device through the continuous slot. In the present exemplary embodiment, the lips of the insertion aid 14 transfer in a curved fashion to the pulling aid 20 provided at the free end of the cylindrical section. The pulling aid 20 is embodied in this exemplary embodiment as a pair of wings extending away from each other. The wings of the pulling aid 20 show a multitude of nubs 21 at the side facing the cylindrical section, resulting in a better feel.

FIG. 6 shows a perspective illustration of another exemplary embodiment. A pulling aid is not provided in this exemplary embodiment. The insertion aid 14 is embodied in a two-part version in this exemplary embodiment, with it being embodied in a first section of the cylindrical section 12, facing the conically tapering section 10, essentially as a lip-like extension of the flanks of the continuous slot 8, curved outwardly. In a second section of the cylindrical section 12, which faces away from the conically tapering section, the insertion aid 14 is embodied in the form of wing-like embodied areas extending away from each other. The areas of the insertion aid 14 extend apart such that on the one hand the insertion of a medical instrument is facilitated and on the other hand a manual spreading of the applicator at the insertion aid 14 is possible. Here, the areas may for example be arranged in reference to each other at an angle from 20 to 90°.

Figure 6A:
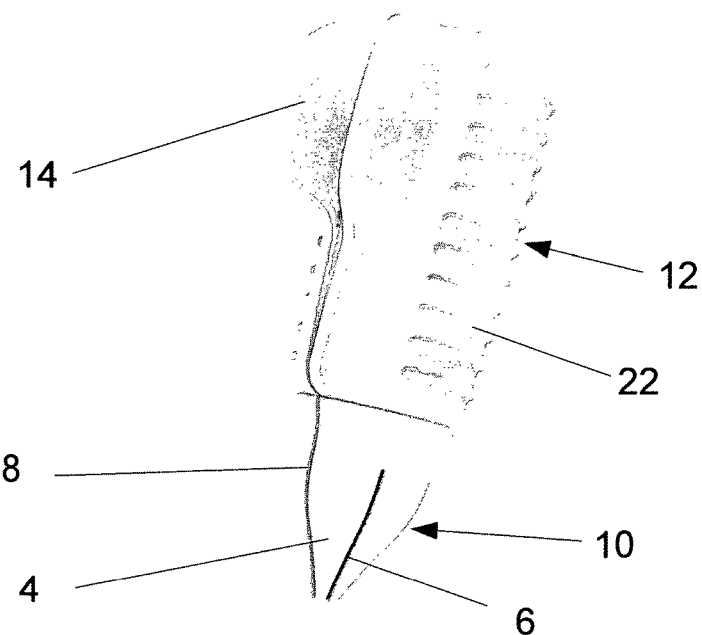
FIG. 6 is a line drawing evidencing a perspective illustration of a. a fourth and b. a fifth exemplary embodiment
Figure 6B:
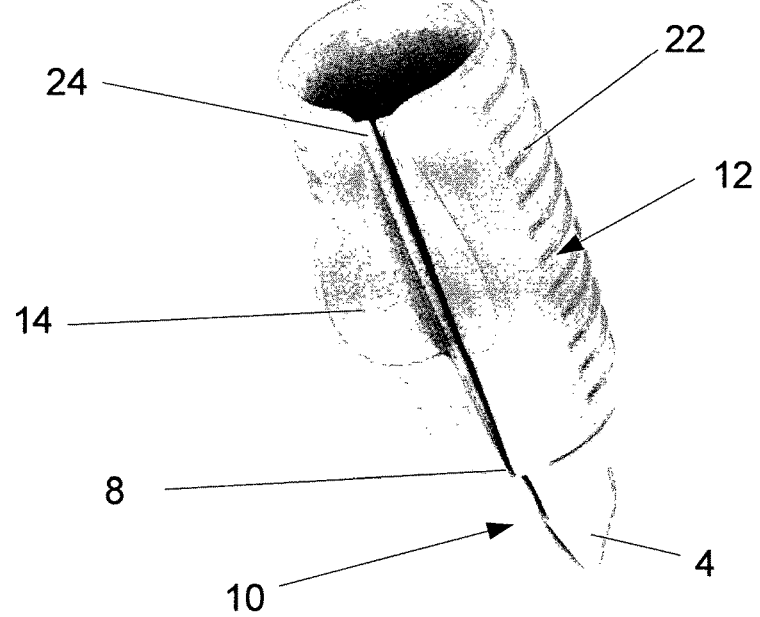

FIG. 6b shows another perspective illustration of another variant of the applicator of FIG. 6a. In this variant, two opposite sealing edges 24 are provided at the continuous slot 8 in the proximity of the insertion aid 14, which constrict the continuous slot in the area of the insertion aid 14 and thus largely prevent the discharge of the composition comprising at least one anti-infectious compound. The sealing edges 24 may comprise the same material as the remainder of the applicator or be connected to the applicator, made from a different material. In the latter case, the material may, e.g., show higher flexibility or elasticity than the one of the applicator. Such an embodiment may be produced in a two-component injection molding process, for example.

When using a two-component injection molding process, here the conically tapering part of the applicator 30 may also be made from a different material, for example showing increased flexibility or elasticity, so that an improved clinging of the tongues 4 to the medical instrument is possible.

Figure 7:
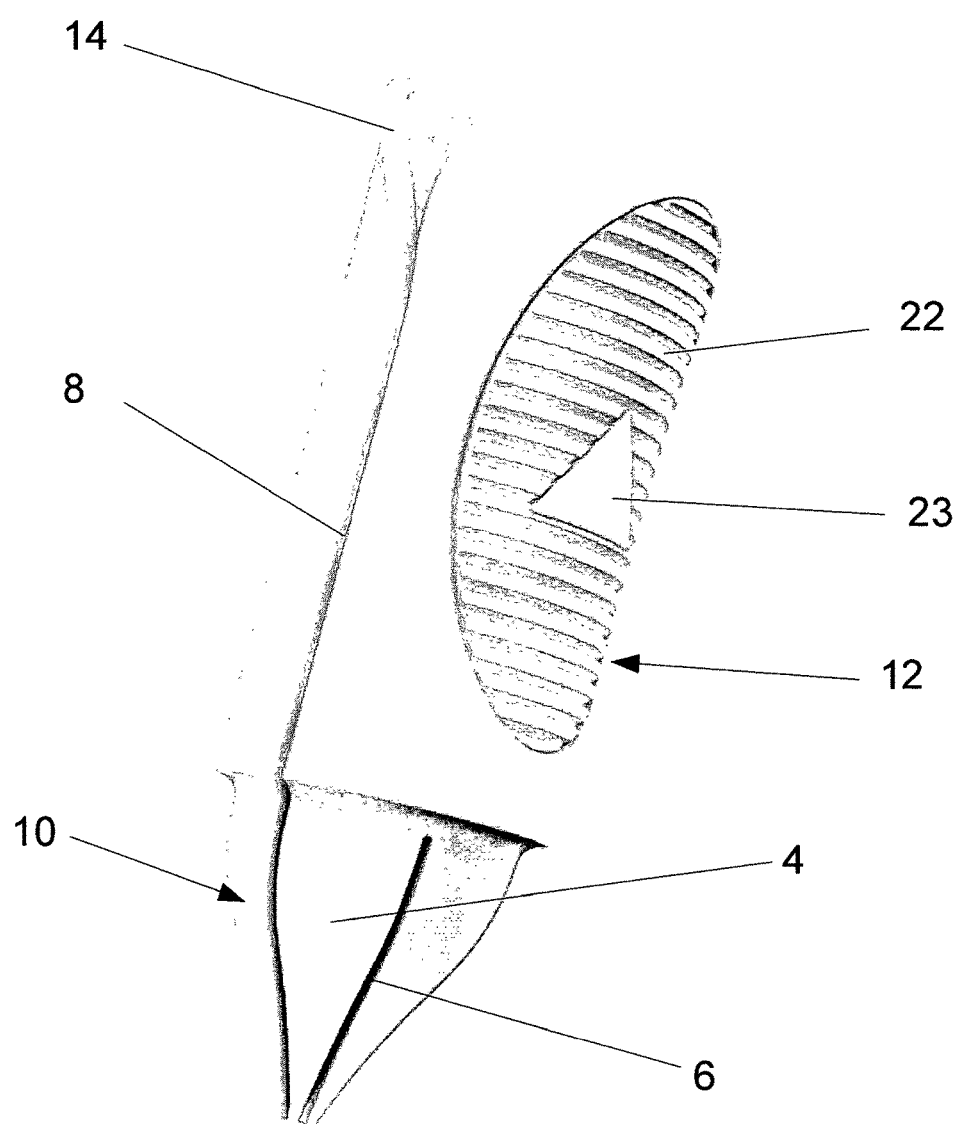
FIG. 7 is a line drawing evidencing a perspective illustration of a sixth exemplary embodiment

FIG. 7 shows a perspective illustration of another exemplary embodiment of an applicator 30, in which the ribs 22 are embodied as a handling zone. The ribs extend perpendicular in reference to the longitudinal direction of the applicator 30 and are arranged parallel. A directional indicator is located in the handling zone, which shows the tensile direction of the applicator when a medical instrument is guided through it. In this exemplary embodiment, the ribs 22 are not embodied as formations on the surface of the applicator, but are formed by inserting a multitude of grooves, extending parallel, into the surface of the applicator.

Additionally, in the present exemplary embodiment, the applicator 30 shows an insertion aid which is embodied as edges of the continuous slot, located at the free end of the cylindrical section and bent outwardly. In other words, a portion of the wall of the cylindrical section located at the edges forms the insertion aid 14 by way of bending.

Figure 8A:
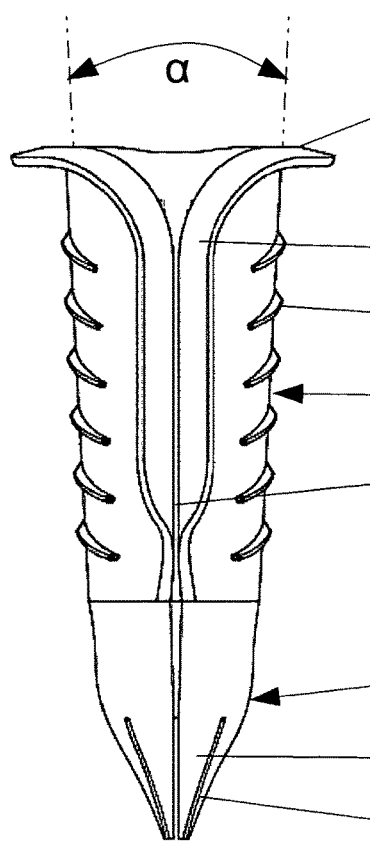
FIG. 8a is a line drawing evidencing a front view and FIG. 8b is a line drawing evidencing a side view of a seventh exemplary embodiment with different conically tapering sections
Figure 8B:
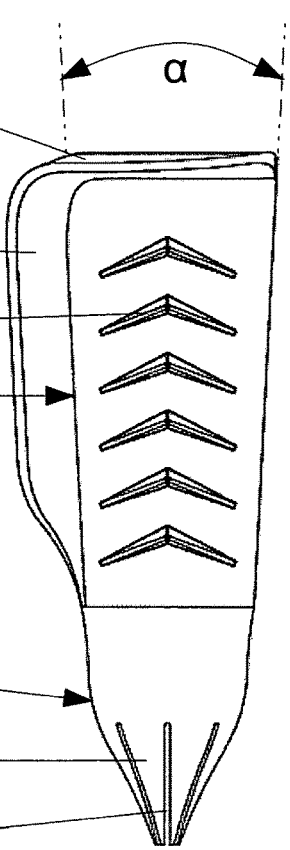

FIG. 8 *a* shows the front view, FIG. 8 *b* the side view of another exemplary embodiment of an applicator 30. In this exemplary embodiment, the applicator comprises two sections 10 and 11, tapering conically to a different extent, with the conically tapering section 10 located in the rear in the direction of motion tapering faster than the conically tapering section 11 located in the front in the direction of motion. This means that an opening angle α is smaller at the end, located in the front in the direction of motion, than the conically tapering section located in the rear in the direction of motion. In the conically tapering section located in the front in the direction of motion, the opening angle amounts to 6°, for example. Due to the fact that the section, located in the front in the direction of motion, is embodied conically, an additional guiding and/or centering of a medical instrument which is used with the applicator is achieved. Further, any filling of the applicator is facilitated, if it has not already been pre-filled, with at least one substance comprising an anti-infectious compound.

A transition from the section, embodied tapering to a greater extent, to the second conical section is formed by adjusting the diameters in the transitional area. Either a staggered or a continuous adjustment of the opening angle alpha can occur.

The conically tapering section located in the rear in the direction of motion is formed with its widest point at the narrowest point of the section located in the front in the direction of motion.

In this embodiment the ribs 22 are embodied as two legs of a triangle, which this way may indicate the direction of motion of the applicator.

Figure 9A:
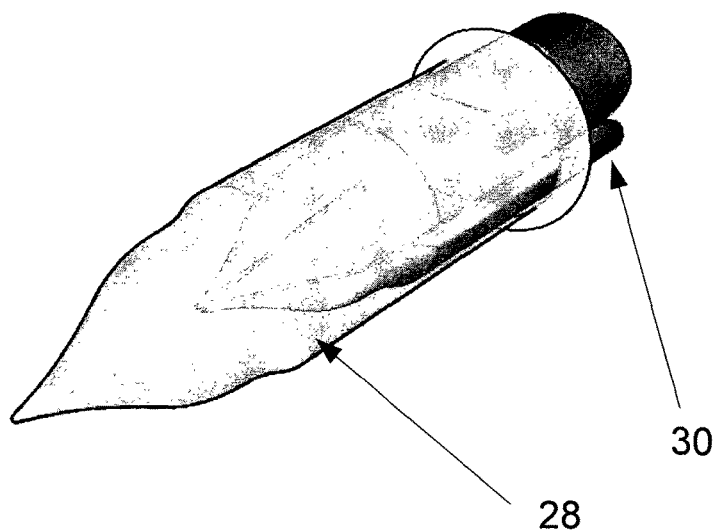
FIG. 9 is a line drawing evidencing an exemplary embodiment with a matching packaging in a. an open and b. a closed state.
Figure 9B:
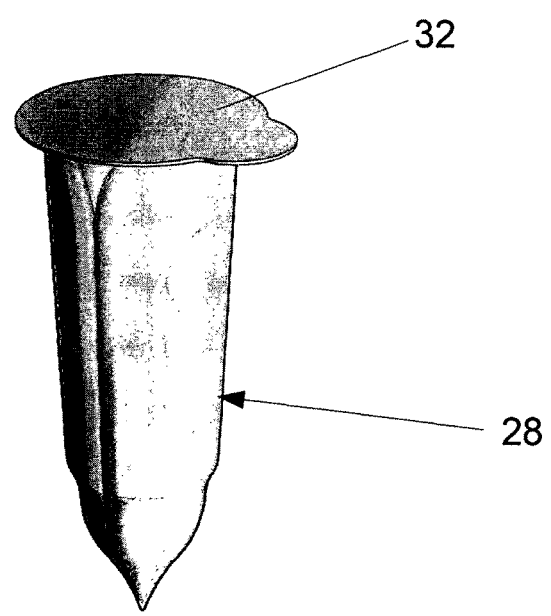

The insertion aid 14 and the pulling aid 20 are embodied transferring into each other and abut the continuous slot 8 as well as the free end of the applicator like a scarf FIG. 9 shows an embodiment of the applicator 30 in connection with a packaging 28. The packaging shows an opening mechanism 32, here in the form of a removable flexible film, e.g., made from metal or plastic.

The material of the applicator is preferably elastic. Various embodiments of the applicator may show two engagement zones 1, into which the thumbs and/or fingers can be inserted in order to hold the applicator and/or in order to apply pressure towards the center. A hollow space 3 is located between the two carriers 2 and/or the two carriers or reservoirs 2, into which a medical instrument, to be inserted into an invasively generated body opening, for example an endoscope, a vascular catheter, or an electrode can be inserted lengthwise. As soon as the medical instrument, e.g., the vascular catheter or the electrode, is located at least partially in the hollow space 3, either a direct contact is generated to the carrier 2 or the reservoir 2 or it is generated by applying pressure towards the inside, originating at the engagement zones 1, due to the thickness of the catheter or the electrode. By pushing or pulling the catheter or the electrode through the hollow space 3 with sufficiently high pressure, a homogenous coating of the catheter or the electrode with a film comprising the composition can be achieved.

The antiseptic composition is applied to or filled into the interior zone and/or the hollow space 3. A catheter or an electrode can either show precisely the diameter of the interior zone 3 or also a larger or smaller diameter. In case of a larger diameter, the elastic material of the applicator is stretched such that the medical instrument, e.g., the catheter or the electrode, fits into the interior zone 3. By rotating the catheter or the electrode, a homogenous film-like coating can be achieved. In case of a smaller diameter, pressure can be applied from the outside, which leads to a compression of the interior zone 3 so that the catheter or the electrode can be coated completely. The pressure may be applied from a top side 5 and/or a bottom side 6 of the applicator, either by applying [pressure] to the respective exterior sides or by engagement zones, which may be arranged in the applicator at the side facing away from the figure.

Normally, 200 to 5000 μl of the composition should be sufficient. The composition may be provided ready to use in a carrier 2 comprising foam or another plastic. The carrier may also be formed from an elastic fibrous material. The entire applicator may also be produced from a single fibrous material, for example at least partially open-pored foam.

EXAMPLES

Example 1

Catheter Contamination in Artificially Infected Fresh Skin with and without Treatment Using the Composition According to the Invention Gel Preparation:

A) Octenidine gel 0.2%

B) Gel foundation: Carbomer 1% (here: Cornegel: (Cornerregel Dexpanthenol 5% in Carbomer 40-60,000 MPas (Bausch & Lomb, Dr. Mann Ph))) viscosity 50,000 mPa s, pH 5.5 adjusted with NaOH, Dexpanthenol addition 5%.

Pig skin with muscles connected to the skin was washed with water and soap. Subsequently, the tissue under the skin was removed such that the underside was sterile. The thickness of the preparation ranged from 3 to 6 mm. Using approximately 200 μl bacteria concentrate (*staphylococcus epidermidis* spp, obtained from fresh pig skin (minipig)) (approx. $0.5\text{-}1\times10^5$ colony forming units per ml)), the epidermis was contaminated over an area of approx. 10×10 cm, the skin was then incubated for 30 min in a culture dish at 37° C. Subsequently, the various gels were applied with an applicator on cannulas and directly thereafter the skin was pierced with them, with a repeated to and fro motion in the injection channel. The cannula was pulled out, the catheter was cut off at the back of the skin in a sterile fashion, the catheter was applied on blood agar, and a Maki-roll[6] was performed with approx. 20 slight impressions in the agar by a simultaneous tapping of the catheter while rolling on the agar.

Subsequently everything was entered into the incubator and incubated and the colonies were counted daily.

Result:

| | Colonies after 1 day | Average |
|---|---|---|
| 1 Catheter without gel | 1271 | 831 |
| 2 Catheter without gel | 211 | |
| 3 Catheter without gel | 492 | |
| 4 Catheter without gel | 1561 | |
| 5 Catheter without gel | 1012 | |
| 6 Catheter without gel | 648 | |
| 7 Catheter without gel | 624 | |
| 8 Catheter with Cornegel-Octenisept (CGO) 0.2% | 12 | 58 |
| 9 Catheter with Cornegel-Octenisept (CGO) 0.2% | 9 | |
| 10 Catheter with Cornegel-Octenisept (CGO) 0.2% | 72 | |
| 11 Catheter with Cornegel-Octenisept (CGO) 0.2% | 16 | |
| 12 Catheter with Cornegel-Octenisept (CGO) 0.2%, very thin skin section, less than 1 mm | 180 | |
| 13 Catheter with Cornegel-Octenisept (CGO) 0.2% | 34 | |
| 14 Catheter with Cornegel-Octenisept (CGO) 0.2% | 82 | |
| 15 Spread above | >3000 | |
| 16 Spread hypoderm after test | 248 | |

The colonies were counted using software (cell explorer 2000) of the co. BioSciTec, Frankfurt.

As discernible from the above table, a 90% reduction of germs could be achieved (from 831 to 58).

Exemplary Embodiment 2

Catheter Contamination in Artificially Infected Fresh Skin with and without Treatment Using the Composition According to the Invention Testing 0.6% ETD2020+2.3% PVP+0.05% octenidine gel in a pigskin model
Gel production of 0.6% ETD2020+2.3% PVP+0.05 octenidine
1.98 g ETD2020+300 ml dH2O (0.66%)
swelling at 60° C. under agitation (>1 h)
adjusting with NaOH to pH 6.3
producing 23% PVP+66.5% dH2O+0.5% octenidine(di)hydrochloride
entering under agitation 10% of the PVP/octenidine mixture to 0.66% gel=
0.6% ETD2020+2.3% PVP+0.05% octenidine
Homogenous mixture, completely clear, no particles discernible.

| Gel components | Manufacturer |
|---|---|
| Carbopol ® ETD2020 NF Polymer | Lubrizol |
| Sodium hydroxide | ROTH |
| Octenidine(di)hydrochloride | Caelo |
| Polyvinyl pyrrolidone K90 M: 360 000 g/mol | ROTH |
| Bi-distilled water | |

Execution of the Experiment/Results:
Approximately 5×6 cm skin was taken from the groin of a pig 10 min after death.
At the day of the experiment the skin was first washed (with water and soap) and then contaminated with approximately 400 µl bacteria concentrate comprising staph *epidermidis* V1815 (1×10⁶/µl), by way of rubbing the concentrate with the finger into the skin.
The entire test arrangement was then placed for 4 h into the incubator at 37° C. (covered with parafilm).
After this, various cannulas were pierced through the skin 6× (control 1-6), cut off in a sterile fashion, and added to blood agar (using an intense Maki-roll, rolling at least four times over the plate and applying approximately 50 slight impressions by way of tapping).

Subsequently the same procedure was performed 6× with cannulas showing a gel coating (gel 7-12) and then the skin was spread.

The plates were then incubated for 16 h in an incubator at 37° C.

| Gel 0.05% | Control | |
|---|---|---|
| 336 | 7000 | |
| 23 | 8000 | |
| 147 | 7000 | |
| 212 | 8000 | |
| 157 | 8000 | |
| 460 | 5000 | |
| 223 | 7167 | Average |
| 154 | 1169 | Stabw |
| 3.10% | 100.00% | % |

Conclusion/Summary:

The plate was counted using a counting program (cell explorer).

Result:

When using the gel the germ count was reduced by almost 2 log levels.

Exemplary Embodiment 3

Catheter Contamination of Artificially Infected Fresh Skin with and without Treatment Using the Composition According to the Invention Testing a germ (V1815 staph *epidermidis*) with 0.1% octenidine in 0.85% carbomer gel (+5% dexpanthenol) on skin in a pigskin model.

| Gel components | Manufacturer |
|---|---|
| Carbopol 980 | OTC Pharma, Bönen |
| Sodium hydroxide | ROTH |
| Octenidine(di)hydrochloride | Caelo |
| Aqua bidest | |
| Sterile cannulas G17, white | B. Braun |

Execution of the Experiment/Results:

Fresh pig skin was contaminated at the top with approximately 60 µl concentrate of staph *epidermidis* V1815 by placing the skin onto the bacteria concentrate in a culture dish. After a 2½ h incubation period at 37° C. in the incubator the skin was mounted on a special syringe box. Apply gel onto the cannula (also the cannulas without any gel as a control), pierce the skin with the cannulas. The cannula is pierced only 1× through the skin (not pulled back), pull out mandrin, cut off in a sterile fashion at the back of the skin, apply agar, and execute an intense Maki-roll (roll 3-4 times over the plate with approximately 50 slight impressions by way of tapping).

Subsequently, the entire arrangement was placed into the incubator and incubated for 14 hours and counted. Photo-documentation. Groups see results:

| Name | Germ count | Average | Stabw |
|---|---|---|---|
| K1_14h | 475 | 990.2 | 763.3 |
| K2_14h | 884 | | |
| K3_14h | 1073 | | |
| K4_14h | 2235 | | |
| K5_14h | 285 | | |
| Gel 6 | 6 | 19.2 | 22.6 |
| Gel 7 | 8 | | |
| Gel 8 | 4 | | |
| Gel 9 | 58 | | |
| Gel 10 | 20 | | |

CONCLUSION/SUMMARY

The plate was counted with the counting program (cell explorer).
Result:
When using the gel the germ count was reduced by almost 2 log stages.

LITERATURE

[1] Wenzel R. and Edmond M. N Engl J Med 2006; 355; 2781-2783

[2] Elek S D, Conen P E, Br J Exp Pathol 1957; 38 (6): 573-86

[3] Hübner N O, Assadian O, Grohmann S A, Diab-Elschahawi M, Kramer A, Efficacy of five alcohol-based skin antiseptics on sebaceous skin used shorter application times the current recommendation of 10 minutes. Eur J Microbiol Infect Dis (2011) 30: 825-829.

[4] Remijsen. Cell Death and Differentiation (2011) 18, 581-588

[5] N. Chaiyakunapruk, D L Veenstra, B A Lipsky, S D Sullivan, S Saint. Vascular Catheter Site Care: The Clinical and Economic Benefits of Chlorhexidine Gluconate Compared with Povidone Iodine. Clinical Infectious Diseases 2003; 37: 764-71

[8] Maki, D. G., C. E. Weise, and H. W. Sarafin. 1977. A semiquantitative culture method for identifying intravenous-catheter-related infection. N. Engl. J. Med. 296: 1305-1309.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

We claim:

1. An applicator for the perioperative disinfection of a medical instrument to be inserted into invasively generated body openings, with the applicator formed as an essentially hollow embodied reservoir with a conically tapering section such that a viscous or foam-like, anti-infectious composition can be retained in the reservoir and applied on a surface of the medical instrument by a relative motion between the applicator and said medical instrument as the medical instrument is guided through the entire length of the applicator and the applicator is located in the rear of the direction of motion.

2. The applicator according to claim 1, which comprises in an interior zone at least one reservoir or at least one carrier for the anti-infectious composition.

3. The applicator according to claim 1, with a cylindrical section following the conical section in the direction of motion.

4. The applicator according to claim 1, wherein the conically tapering section and/or the cylindrical section are open at the front end, seen in the direction of motion.

5. The applicator according to claim 1, with a retention device for the anti-infectious compound comprising an opening, which is additionally slotted.

6. The applicator according to claim 1, with the conically tapering section comprising a multitude of slots, embodied in the axial direction starting at the rear end of the conical section, seen in the direction of motion.

7. The applicator according to claim 1, with the conically tapering section essentially showing the form of a frustum.

8. The applicator according to claim 7, with a multitude of flexible tongues being formed by the slots.

9. The applicator according to claim 1, wherein the reservoir or the carrier are filled with a viscous, anti-infectious composition.

10. The applicator according to claim 1, with the applicator comprising laterally a slot, continuous in the axial direction.

11. The applicator according to claim 1, with the applicator comprising an insertion aid for the medial instrument at a continuous slot extending laterally in the axial direction.

12. The applicator according to claim 1, wherein at least two engagement zones are provided at its exterior.

13. The applicator according to claim 1, further comprising an anti-infectious composition wherein the composition is embodied to adhere on the medical instrument like a film after being brought into contact with the medical instrument, and that at least a portion of the composition adhering like a film reaches at least to the epidermis upon insertion of the medical instrument into the body.

14. The applicator according to claim 13, further comprising a vascular catheter.

* * * * *